United States Patent
Riley et al.

(10) Patent No.: US 8,569,556 B2
(45) Date of Patent: Oct. 29, 2013

(54) METHOD FOR CONTROLLING 2-PHENYL ISOMER CONTENT OF LINEAR ALKYLBENZENE AND CATALYST USED IN THE METHOD

(71) Applicant: UOP LLC, Des Plaines, IL (US)

(72) Inventors: Mark G. Riley, Hinsdale, IL (US); Deng-Yang Jan, Elk Grove Village, IL (US); Stephen W. Sohn, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/779,172

(22) Filed: Feb. 27, 2013

(65) Prior Publication Data

US 2013/0178678 A1 Jul. 11, 2013

Related U.S. Application Data

(62) Division of application No. 12/881,676, filed on Sep. 14, 2010, now Pat. No. 8,389,785.

(51) Int. Cl.
*C07C 2/66* (2006.01)

(52) U.S. Cl.
USPC .......................................... 585/455; 585/467

(58) Field of Classification Search
USPC .................................................. 585/455, 467
See application file for complete search history.

(56) References Cited

U.S. PATENT DOCUMENTS

2009/0062583 A1* 3/2009 Guillon et al. ................ 585/301

* cited by examiner

*Primary Examiner* — Thuan D Dang
(74) *Attorney, Agent, or Firm* — Arthur E Gooding

(57) ABSTRACT

A method for controlling 2-isomer content in linear alkylbenzene obtained by alkylating benzene with olefins and catalyst used in the method.

3 Claims, 1 Drawing Sheet

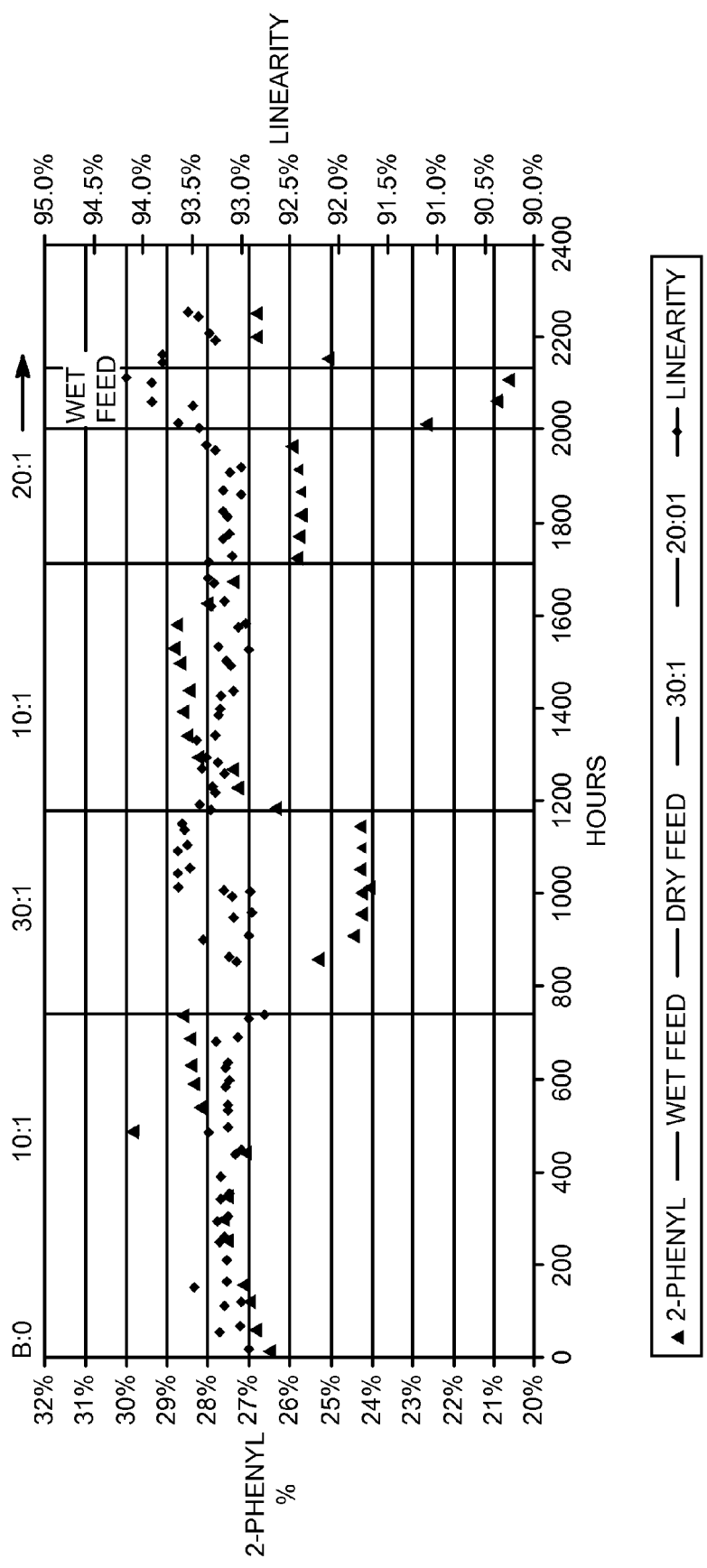

METHOD FOR CONTROLLING 2-PHENYL ISOMER CONTENT OF LINEAR ALKYLBENZENE AND CATALYST USED IN THE METHOD

CROSS-REFERENCE TO RELATED APPLICATION

This application is a Division of prior copending application Ser. No. 12/881,676 which was filed on Sep. 14, 2010, the contents of which are incorporated herein by reference thereto.

FIELD

The invention relates generally to alkylation of aryl compounds with olefins. More particularly, the invention relates to a method for controlling 2-isomer content in linear alkylbenzene obtained by alkylating benzene with olefins. The invention also relates to the catalyst used in the method.

DESCRIPTION OF RELATED ART

Linear alkylbenzenes (LAB) are compounds that have significant commercial importance. Linear alkylbenzene sulfonate (LAS) compounds made by sulfonation of linear alkylbenzene are used in the manufacture of detergents and other products. Because linear alkylbenzenes are more easily biodegradable than branched alkylbenzenes, linear alkylbenzenes have essentially replaced branched alkylbenzenes in detergents and other products. In particular, linear alkylbenzenes with long alkyl chains, such as chains having about 10 to about 14 carbons, are commonly used. However, linear alkylbenzenes with longer chains and with shorter chains also are commercially important.

Linear alkylbenzenes often are made by alkylation of benzene with olefins. Positional isomers, such as 2-phenyl, 3-phenyl, 4-phenyl, 5-phenyl, and the like, result from this alkylation of benzene with long chain olefins. The distribution of the phenyl along the alkyl chain produces different products.

Historically, linear alkylbenzenes are manufactured commercially using classic Friedel-Crafts condensation employing catalysts such as aluminum chloride, or by using strong acid catalysts such as hydrogen fluoride, for example, to alkylate benzene with olefins. In 1995, a solid bed alkylation process, the Detal™ process, using a solid non-corrosive acid catalyst was introduced. While such methods produce high conversions, the selectivity to the 2-phenyl isomer typically is about 30 percent or less. Linear alkylbenzenes with a high percentage of the 2-phenyl isomer are highly desired because such compounds when sulfonated have long tails that provide enhanced solubility and detergent properties.

The 2-phenyl isomer content of the product is process dependent. Solid alkylation catalysts, such as those used in the Detal™ process, produce products with 2-phenyl isomer content between 25 and 30 percent. HF-catalyzed processes typically yield a 2-phenyl isomer content less than 20 percent, and $AlCl_3$ typically between 30 and 33 percent. The properties of linear alkylbenzenes and linear alkylbenzene sulfonate produced from these three processes have been disclosed by Berna and coworkers in the following publications. *Journal of Surfactants and Detergents*, Vol. 3, No. 2 (July 2000) pages 353 through 359, *JAOCS*, Vol. 72, No. 1 (1995) pages 115 through 122, and *Tenside Surfactants Detergents* 25 (1988) 4, pages 216 through 221. Typical distributions of the positional isomers in products produced by the process are summarized in the following table:

TABLE 1

| Catalyst | 2-φ (%) | 3-φ (%) | 4-φ (%) | 5-φ (%) | 6-φ (%) |
|---|---|---|---|---|---|
| ZSM-12 | 92 | 8 | 0 | 0 | 0 |
| Mordenite | 85 | 15 | 0 | 0 | 0 |
| Offretite | 79 | 14 | 5 | 1 | 1 |
| ZSM-4 | 57 | 25 | 8 | 5 | 5 |
| Beta | 57 | 18 | 10 | 7 | 8 |
| Linde L | 40 | 18 | 16 | 15 | 11 |
| ZSM-38 | 37 | 19 | 13 | 14 | 16 |
| ZSM-20 | 51 | 21 | 11 | 9 | 8 |
| REY | 25 | 20 | 18 | 19 | 18 |
| HF | 20 | 17 | 16 | 23 | 24 |
| $AlCl_3$ | 32 | 22 | 16 | 15 | 15 |

Zeolite catalysts also have been used to obtain linear alkylbenzenes by alkylation of benzene with olefins. The 2-phenyl isomer content of linear alkylbenzenes obtained using such catalysts depends on the zeolite selected and can vary from about 20 percent to 90 percent. However, some zeolytic catalysts are quickly deactivated, and very high concentration of 2-phenyl isomer in linear alkylbenzene yields a linear alkylbenzene sulfonate that dissolves poorly in water. Most zeolites, with the exception of FAU, produce linear alkylbenzene with 2-phenyl isomer content higher than existing commercial processes.

The differences in linear alkylbenzene compositions produce different linear alkylbenzene sulfonate products. The products differ not only in composition but also in properties and characteristics. Some of the properties that detergent formulators need to consider are solubility, viscosity, detergency performance, foaming power, foam stability, hard water stability, and biodegradability. A number of these properties are dependent on the isomeric composition of the linear alkylbenzene sulfonate.

Thus, there exists a need for a method for controlling 2-phenyl isomer content of linear alkylbenzenes obtained by alkylating benzene with olefins.

SUMMARY OF THE INVENTION

Aspects of this invention relate to alkylation of aryl compounds with olefins. In particular, embodiments of the invention are directed to a method for alkylation of benzene with olefins to obtain linear alkylbenzenes.

Embodiments of the invention are directed to a method for controlling 2-phenyl isomer content of linear alkylbenzenes obtained by alkylating benzene with olefins.

Other embodiments of the invention are directed to catalyst used in the method for controlling 2-phenyl isomer content of linear alkylbenzene obtained by alkylating benzene with olefins.

BRIEF DESCRIPTION OF THE DRAWINGS

FIG. 1 illustrates the 2-phenyl isomer content of linear alkylbenzenes obtained in accordance with embodiments of the invention.

DETAILED DESCRIPTION

Embodiments of the invention provide a method for alkylation of aryl compounds with olefins. Aryl compounds typically are selected from the group consisting of toluene, xylene, benzene, and mixtures thereof. Most typically, embodiments of the invention relate to alkylation of benzene. For convenience, the invention will be described as it relates to benzene, but extends to other aryl compounds.

Embodiments of the invention relate to alkylation of benzene with olefins to obtain linear alkylbenzenes. Linear alkylbenzenes are commercially important products that are a mixture of positional isomers. However, certain positional isomers are preferred for some uses. For example, 2-phenyl isomer, particularly ones made with a straight-chain olefins having at least about 10 carbon atoms, are preferred for use in making linear alkylbenzene sulfonate for use in liquid detergent manufacture. The 2-phenyl isomers provide enhanced water solubility, which aids in the formulation of liquid detergent. For powdered detergents, high and low 2-phenyl formulations perform equally well.

Typically, linear alkylbenzenes are manufactured commercially using classic Friedel-Crafts condensation or catalysis with strong acid to alkylate benzene with olefins. However, these reactions typically yield linear alkylbenzene products that contain about 25 to about 33 percent, and less than about 22 percent, respectively, of the 2-phenyl isomer.

Most zeolite catalysts yield linear alkylbenzene products containing more than about 40 percent 2-phenyl isomer, but such a high 2-phenyl isomer content falls outside the 2-phenyl range of commercial detergent formulations. RE-Y zeolite is suitable for producing linear alkylbenzene having properties and characteristics like linear alkylbenzenes produced using HF catalyst, but no individual zeolite is known that produces high 2-phenyl isomer content linear alkylbenzene of quality similar to linear alkylbenzene products of the Detal™ process or $AlCl_3$.

Importantly, the producer is not able to control the 2-phenyl isomer content to produce a consistent product having a selected 2-phenyl isomer content for any of these methods. The 2-phenyl isomeric content has been a function of the process the producer uses to produce the linear alkylbenzene.

The skilled practitioner recognizes that one work around to the lack of a single zeolite with the correct properties is to use different zeolites in separate reaction zones and blend the production from each reaction zone to meet 2-phenyl content and other desired linear alkylbenzene product properties. In this way, 2-phenyl isomeric content can be adjusted by varying the amount of linear alkylbenzene produced over each catalyst. Examples of such methods are described in U.S. Pat. No. 7,297,826 and U.S. Pat. App. Pub. No. 2009/0062583. While techniques that blend products form separate reaction zones or reactors can be used to produce linear alkylbenzene, they are more complicated than those using a single catalyst. All existing commercial linear alkylbenzene plants use a single alkylation catalyst.

The inventors have discovered that it is possible to control the 2-phenyl isomer content of linear alkylbenzene obtained by alkylation of benzene with olefins. Embodiments of the invention are directed to a method for controlling 2-phenyl isomer content of linear alkylbenzenes obtained by alkylating benzene with olefins. Other embodiments of the invention are directed to catalyst used in the method for controlling 2-phenyl isomer content of linear alkylbenzene obtained by alkylating benzene with olefins.

Embodiments of the invention provide a number of advantages. In accordance with embodiments of the invention, it is possible to produce linear alkylbenzene having a selected 2-phenyl isomer content. Further, embodiments of the invention make it possible to compensate for changes in feedstock composition, particularly for changes in benzene to olefin (B:O) ratio, to obtain a linear alkylbenzene product having a preselected 2-phenyl isomer content. As used herein, 'feed' or 'feedstock' means the same as 'process stream,' and is not limited to only fresh feed, but rather includes any recycled materials.

Other embodiments of the invention are directed to catalyst used in the method for controlling the 2-phenyl isomer content of linear alkylbenzene. Thus, embodiments of the invention enable the producer to produce a linear alkylbenzene product having a preselected 2-phenyl isomer content.

In accordance with embodiments of the invention, catalyst comprises two acidic components. A first catalyst component produces lower 2-phenyl isomer content linear alkylbenzene, and a second catalyst component produces higher 2-phenyl isomer content linear alkylbenzene. As used herein, the lower 2-phenyl isomer catalyst component would itself produce a 2-phenyl isomer content less than about 23 percent, and the higher 2-phenyl isomer content catalyst component would itself produce a 2-phenyl isomer content greater than about 30 percent.

In embodiments of the invention, the first catalyst component is selected from the group consisting of rare earth-containing faujasites and blends thereof, and the second catalyst component is selected from any solid acidic material suitable for production of linear alkylbenzene having high 2-phenyl isomer content.

As the skilled practitioner recognizes, a faujasite is a type of catalyst for which the abbreviation FAU has been established by the International Zeolite Association. The International Zeolite Association recognizes framework types, classifies them and assigns three-letter codes, and summarizes selected properties and characteristics for the frameworks.

In accordance with embodiments of the invention, the first catalyst component is a zeolite selected from the group consisting of rare-earth containing faujasites and blends thereof. In particular embodiments of the invention, the first catalyst component is a zeolite selected from the group consisting of X-type faujasite doped with a rare earth element, Y-type faujasite doped with a rare earth element, and blends thereof. The skilled practitioner recognizes that these catalysts often are abbreviated RE-X and RE-Y.

In accordance with embodiments of the invention, the rare earth component of the faujasite catalyst is selected from the group consisting of the elements having an atomic number from 57 to 71 and blends thereof. The elements having an atomic number in this range also are known as the Lanthanides. Typically, the rare earth component is selected from the group consisting of lanthanum, cerium, preseodymium, neodymium, other rare earths typically associated with the named rare earths, and blends thereof. Often, a mixture of rare earth elements is used because such mixtures are commercially available and are more cost-effective than purified elements. The skilled practitioner recognizes that other rare earths are present with the identified rare earths and are not separated therefrom because it is not cost-effective to do so.

The rare earth element component comprises greater than about 16.5 percent of the RE-Y weight, typically between about 16.5 percent and about 18 percent, and more typically between about 16.5 percent and about 17.5 percent. Most typically, the rare earth element component comprises at least about 16.5 percent of the RE-Y zeolite component weight.

The second catalyst component is a solid acidic material suitable for production of high 2-phenyl isomer linear alkylbenzene. Typically, the second catalyst component is zeolite selected from the group consisting of UZM-8, Zeolite MWW, Zeolite BEA, Zeolite OFF, Zeolite MOR, Zeolite LTL, Zeolite MTW, BPH/UZM-4, and blends thereof. Properties and characteristics of UZM-8, and a method for manufacturing it, are disclosed in U.S. Pat. No. 6,756,030, the entirety of which is hereby incorporated by reference. Typically, one starts with the $NH_4$ form of UZM-8, which decomposes to the hydrogen form upon calcination. The other zeolites are zeolites identified by International Zeolite Association framework identification codes.

More typically, therefore, the second catalyst component is selected to have moderate acidity. Moderate acidity allows the water to be removed from the zeolite under mild drying conditions, thus restoring the activity of this second catalyst compound. Highly acidic zeolites such as MOR or BEA release water more slowly than moderately acidic zeolites such as UZM-8 or MCM-22 under the same conditions. In addition, moderately acidic zeolites tend to cause less skeletal isomerization of the olefin, which leads to a more linear product.

Because zeolites having moderate acidity have preferred properties and characteristics for use as a high 2-phenyl isomer content catalyst component, more typically the second catalyst component is zeolite selected from the group consisting of UZM-8, Zeolite MWW, Zeolite LTL, and blends thereof. Most typically, the second catalyst component is zeolite selected from the group consisting of UZM-8, MWW, and blends thereof.

There are practical reasons to choose moderately acidic zeolite that produces linear alkylbenzene having a 2-phenyl isomer content between about 30 and about 50 percent to formulate the catalysts. Zeolites with these characteristics will constitute a greater proportion of a catalyst than a high acidity zeolite designed to achieve the same 2-phenyl isomer content. Using a greater proportion of moderate acidity zeolites is preferable to using a lesser proportion of high acidity zeolites because it leads to a more robust catalyst formulation. For example, if a catalyst formulated with 10 percent MOR yields the same 2-phenyl isomer content as a catalyst formulated with 30 percent UZM-8, then a 0.1 percent error, based on the total weight on the catalyst, in the amount of MOR in the catalyst has more impact on the 2-phenyl isomer content then the same 0.1 percent error would have on the 2-phenyl isomer content of product formulated with UZM-8. That is, the 0.1 percent error, based on the total weight of the catalyst, in MOR is a 1 percent error (0.1/10) in the catalyst of composition. However, the same 0.1 percent error in UZM-8 is only a 0.33 percent error (0.1/30.0) in catalyst composition.

The use of zeolites that produce very high 2-phenyl isomer content also introduces another formulation disadvantage. The two zeolite components of the catalyst typically will not deactivate at exactly the same rate. Deactivation of a zeolite that produces very high 2-phenyl isomer content will have a much greater impact on the 2-phenyl isomer content than deactivation of a moderate acidity zeolite. Thus, use of a moderate acidity zeolite that produces isomer content close to a selected, or target, 2-phenyl isomer content is preferred. With the guidance provided herein, the skilled practitioner will be able to select an acid catalyst for catalyst formulation.

Catalyst embodiments of the invention are formulated to yield linear alkylbenzene products having between about 15 percent and about 45 percent 2-phenyl isomer, typically between about 20 percent and about 40 percent 2-phenyl isomer, and more typically between about 25 percent and about 35 percent 2-phenyl isomer.

The relative proportion of first catalyst component and second catalyst component is selected so that, under dry operating conditions, the catalyst produces linear alkylbenzene having target, or pre-selected, 2-phenyl isomer content at about a 30:1 molar ratio of benzene to olefin (B:O) in the feed. Dry operating condition is defined herein as 'bone dry', or less than about 5 ppm water in the feed. Dry operating condition ensures that the acidic sites on the second catalyst component are active and available to produce linear alkylbenzenes having high 2-phenyl isomer content.

Catalyst embodiments of the invention that yield a selected 2-phenyl isomer content in linear alkylbenzenes produced by alkylation of benzene with olefin in the presence of the catalyst under dry operating conditions with a B:O ratio of about 30:1 comprise proportions of first and second catalyst components that are related to the properties and characteristics of the components and to the selected 2-phenyl isomer content. Typically, catalyst embodiments of the invention comprise between about 30 percent and about 70 percent of first catalyst component, based on the total weight of the catalyst components. More typically, the fraction of the catalyst that is first catalyst component is between about 45 percent and about 65 percent, most typically between about 50 percent and about 60 percent, based on the total weight of catalyst components.

Na—Y is commonly available and is produced by nearly every zeolite manufacturer. RE-Y is made by multiple ion exchange of Na—Y with rare earth chloride or nitrate salts in accordance with techniques will know to those skilled in the art. Multiple ion exchange steps are typically required to achieve the level of RE exchange required for this invention.

UZM-8 can be produced according to a method disclosed in U.S. Pat. No. 6,756,030, the entirety of which is hereby incorporated by reference. The ammonium form of UZM-8 is made by ion exchange of Na-UZM-8 with an ammonium salt by techniques known to those skilled in the art.

The catalyst components are in the form of powders. The catalyst embodiments of the invention are made in a manner that yields solid catalyst particles comprising both catalyst components. Typically, the first catalyst component and the second catalyst component are mixed with a binder. Typical binders include clay and alumina, and other binders are known to the skilled practitioner. Fluid, typically water or another suitable solvent is added to the mixture of binder and catalyst components in quantity suitable to form an extrudable paste.

Catalyst in accordance with embodiments of the invention then is formed by extruding the paste to form solid catalyst of embodiments of the invention. Solid catalyst may be in the form of pellets, cylinders, or any suitable form. With the guidance provided herein, the skilled practitioner will be able to prepare suitable solid catalyst.

In accordance with embodiments of the invention, benzene is alkylated with olefin in the presence of the catalyst described herein to produce linear alkylbenzenes having a selected a 2-phenyl isomer content. The 2-phenyl isomer content is controlled by controlling the concentration of water in the feed or process stream.

At dry operating condition, the high 2-phenyl isomer content is obtained. Further, the inventors have discovered that, at operating condition other than dry operating condition, the 2-phenyl isomer content obtained is lower than the high 2-phenyl isomer content. Although the inventors do not wish to be bound by theory, it is believed that water in the process stream neutralizes some of the acidity of the high acidity catalyst component and reduces the activity of that component. Also, it is believed that the low 2-phenyl isomer catalyst component becomes relatively more active because the water produces additional reaction-catalyzing sites, as described below, thus reducing the 2-phenyl isomer content of the resultant linear alkylbenzene.

In accordance with embodiments of the invention, the concentration of water in the feed is controlled to control the 2-phenyl isomer content of the linear alkylbenzene. At wet operating condition, which is defined herein as a water concentration of about 100 ppm in feed, linear alkylbenzene having the low 2-phenyl isomer content is produced. Embodiments of the invention are directed to controlling the 2-phenyl isomer content of linear alkylbenzene thus produced by controlling the water concentration in the feed between dry operating condition and wet operating condition. In these embodiments of the invention, changing the water concentration in the feed changes the 2-phenyl isomer content of the linear alkylbenzene. Dry operating condition, i.e., low dew point, yields high 2-phenyl isomer content linear alkylbenzene, whereas wet operating condition, i.e., high dew point, yields low 2-phenyl isomer content linear alkylbenzene.

Embodiments of the invention afford the opportunity to adjust the 2-phenyl isomer content between the low 2-phenyl isomer content and the high 2-phenyl isomer content for which the catalyst is designed by adjusting the water concentration in the feed between bone dry, i.e., less than about 5 ppm, and about 100 ppm. The operating condition can be changed at will to control the 2-phenyl isomer content.

Although the inventors do not wish to be bound by theory, it is believed that water in the process stream neutralizes some of the high 2-phenyl isomer catalyst component and simultaneously enhances acidity of the low 2-phenyl isomer catalyst component, such as rare earth faujasite, by creating additional Brönsted acid sites. It is believed that these sites are created when the OH⁻ moiety from water associates with the rare earth element and the H⁺ moiety associates with a lattice oxygen on the zeolite. This effect is easily reversible.

Therefore, to increase 2-phenyl isomer content in accordance with embodiments of the invention, the feed water concentration is reduced. Reducing the feed water concentration will allow the opportunity to remove adsorbed water from the zeolites and dry the catalyst. Then, the acidity of the high acid, high 2-phenyl isomer catalyst component increases and the acidity of the low 2-phenyl isomer catalyst component decreases.

Water concentration in the process stream can be adjusted as part of the typical benzene dehydration step, or in any convenient way. For example, water can be added by way of a water injection pump. Water can be desorbed from the catalyst during the catalyst regeneration cycle. Excess water is removed from the system at the benzene distillation column. The skilled practitioner will, with the guidance provided herein, be able to adjust the water concentration in the process stream to control the 2-phenyl isomer content in the product linear alkylbenzene.

Linearity, i.e., the percentage of linear alkylbenzene produced that contains a linear alkyl chain, also is an important criterion for evaluating catalysts. Linearity of linear alkylbenzene produced with embodiments of the invention is essentially constant, with very litter variation caused by process stream water concentration or B:O ratio, for example.

Embodiments of the invention are directed to alkylation of benzene with olefins to produce linear alkylbenzene having a selected 2-phenyl isomer content. The skilled practitioner recognizes that suitable benzene and olefin feedstocks can be obtained from many sources, and that the resultant product stream may contain by-products, such as heavy alkylates or bi-alkylates, paraffins, and other products. The feedstocks can be prepared and by-products can be removed from the product stream in accordance with methods known to the skilled practitioner.

The invention provides a process for the production of linear alkylbenzenes from a substantially linear olefin having from 8 to 28 carbon atoms with an aromatic hydrocarbon feedstream in the presence of a catalyst under reaction conditions.

An embodiment of the present invention is a process that uses two feedstocks, a substantially linear (non-branched) olefin and an aryl compound. The linear olefin can be a mixture of linear olefins with double bonds at terminal and internal positions or a linear alpha olefin with double bonds located at terminal positions. The linear olefin comprises molecules having from 8 to 28 carbon atoms, typically from 8 to 15 carbon atoms, and more typically from 10 to 14 carbon atoms. As noted above, for convenience, the invention is described herein as it relates to benzene.

The olefin and aryl compounds are reacted in the presence of a catalyst under reaction conditions. The reaction conditions for alkylation are selected to minimize isomerization of the alkyl group and minimize polyalkylation of the benzene (or aromatic moiety of other aryl compounds), while trying to maximize the consumption of the olefins to maximize product. Alkylation conditions include a reaction temperature between about 50° C. and about 200° C., and typically between about 80° C. and about 175° C. The pressures in the reactor are from about 1.4 MPa (203 psia) to about 7 MPa (1015 psia), and preferably from about 2 MPa (290 psia) to about 3.5 MPa (507 psia). The reaction is carried out in the liquid phase and the pressure is always high enough to have a single phase at reaction temperature. To minimize polyalkylation of the benzene, the B:O ratio is between about 2.5:1 and about 50:1, and typically between about 5:1 and about 35:1. The average residence time in the reactor helps control product quality, and the process is operated at a liquid hourly space velocity (LHSV) from about $0.1\ hr^{-1}$ to about $30\ hr^{-1}$, with a preferred LHSV between about $0.3\ hr^{-1}$ and about $6\ hr^{-1}$.

The olefins can be produced from the dehydrogenation of paraffins, cracking of paraffins and subsequent oligomerization of smaller olefinic molecules, or other known processes for the production of linear monoolefins. The separation of linear paraffins from a mixture comprising normal paraffins, isoparaffins, and cycloparaffins for dehydrogenation can include the use of known separation processes, such as the use of UOP Sorbex™ separation technology. UOP Sorbex™ technology can also be used to separate linear olefins from a mixture of linear and branched olefins.

A method for the production of the paraffinic feedstock is the separation of linear (nonbranched) hydrocarbons or lightly branched hydrocarbons from a kerosene boiling range petroleum fraction. Several known processes that accomplish such a separation are known. One process, the UOP Molex™ process, is an established, commercially proven method for the liquid-phase adsorption separation of normal paraffins from isoparaffins and cycloparaffins using the UOP Sorbex™ separation technology.

Paraffins can also be produced in a gas to liquids (GTL) process, where synthesis gas made up of CO and $H_2$ at a controlled stoichiometry are reacted to form larger paraffinic molecules. The resulting paraffinic mixture can then be separated into normal paraffins and non-normal paraffins, with the normal paraffins dehydrogenated to produce substantially linear olefins.

In the process of producing olefins from paraffins, by-products include diolefins and alkynes, or acetylenes. The streams comprising diolefins and acetylenes are passed to a selective hydrogenation reactor, where the diolefins and alkynes are converted to olefins.

The reaction conditions, including the B:O ratio, typically are set to obtain complete reaction of olefins while minimizing polyalkylation and other reactions that reduce linear alkylbenzene yield and introduce impurities. However, the B:O ratio has a weak influence on 2-phenyl isomer content. For example, a catalyst that will yield a selected 2-phenyl isomer content at a B:O ratio of 30:1 will yield a higher 2-phenyl isomer content at a B:O ratio of 10:1. However, in accordance with embodiments of the invention, the 2-phenyl isomer content can be reduced to achieve the target 2-phenyl isomer content by injection of water.

Each of the effects described herein are illustrated in FIG. 1, as described in the following example.

EXAMPLE 1

Catalyst comprising 56 percent RE-Y having a rare earth content of 17.0 percent rare earths, primarily La, Nd, Ce, Pr, and Sm, based on the weight of the RE-Y zeolite, and 24 percent, based on the total weight of zeolite and binder, of UZM-8 zeolite, was prepared using 20 percent, based on the total weight of zeolite and binder, of alumina as binder. The catalyst was extruded as a 1/16" cylinder.

Benzene and Pacolate™ olefin-containing product from a commercial Detal™ process complex were reacted under typical constant alkylation conditions. The Pacolate™ olefin-containing product had approximately 10 percent $C_{10}$-$C_{13}$ normal olefins in n-paraffins of the same carbon number range. B:O ratio and water in the process stream were changed as follows:

| Hours on stream | Feed type | B:O molar ratio |
|---|---|---|
| 0 | Dry | 10:1 |
| 741 | Dry | 30:1 |
| 1176 | Dry | 10:1 |
| 1712 | Dry | 20:1 |
| 2000 | Wet | 20:1 |
| 2121 | Dry | 20:1 |

Note:
Dry feed was bone dry, i.e., had less than about 5 ppm water
Wet feed had about 100 ppm water The LHSV typically was between 2.4 and 3.1, with few cycles at LHSV=3.75. LHSV was adjusted to maintain the rate of olefins passing over the catalyst to remain constant as the B:O ration changed. Process temperature was 135° C. and regeneration temperature was about 250° C. for most cycles, and was reduced to 225° C. for the last cycles.

The 2-phenyl isomer content obtained, as a percentage of linear alkylbenzene, and linearity, also as a percentage of linear alkylbenzene, as a function of B:O ratio, moisture in feed, and hours of operation, is illustrated in FIG. 1. As can be seen, B:O ratio had a weak effect on 2-phenyl isomer content, which ranged from about 28 percent at B:O ratio of 10:1, to about 26 percent at B:O ratio of 20:1, and to about 24 percent at B:O ratio of 30:1. Although the inventors do not wish to be bound by theory, this behavior is believed to be due to the concentration's impacting olefin double bond isomerization, olefin skeletal isomerization, and olefin alkylation in different ways. The rates of monomolecular reactions, olefin double bond isomerization and skeletal isomerization, increase as B:O ratio decreases (olefin concentration increases). The rate of the bimolecular reaction, olefin alkylations, decreases as B:O ratio decreases. 2-phenyl linear alkylbenzene is obtained when 1-olefins and 2-olefins are alkylated. Since 1-olefins are more reactive than internal olefins, higher 2-phenyl linear alkylbenzene yields are expected when the rate of olefin double bond isomerization is high relative the rate of alkylation. It is believed that this is what is observed at lower B:O ratios.

FIG. 1 also illustrates that 2-phenyl isomer content was about 26 percent at B:O ratio of 20:1 for both dry feed periods, with a wet feed period interposed. The 2-phenyl isomer content was between about 20 percent and about 21 percent with wet feed. Thus, the transition from dry feed to wet feed reduced 2-phenyl isomer content from about 26 percent to between about 20 percent and about 21 percent, and the transition back to dry feed was the 2-phenyl isomer content return to about 26 percent. Additional cycles in which feed water content and B:O ratio were varied produced results consistent with the reported results.

Also, linearity was consistently between about 93.0 percent and 94.0 percent throughout this operation.

This example should be considered illustrative of embodiments of the invention, and should not be used to limit the invention in any way.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims. For example, embodiments of the invention can be directed to aryl compounds other than benzene, such as toluene and xylene.

The invention claimed is:

1. A process for alkylating a benzene with an olefin comprising reacting a substantially linear olefin having at least 10 carbon atoms with a benzene under alkylation reaction conditions in the presence of a catalyst to produce alkylated benzene, said catalyst comprising a first catalyst component containing faujasite comprises at least about 16.5 wt. percent rare earth selected from the group consisting of lanthanum, cerium, praseodymium, neodymium, other rare earths typically associated with the named rare earths, and blends thereof, and a second catalyst component zeolite selected from the group consisting of UZM-8; wherein the alkylation reaction is operated in the presence of water, and the water content is maintained in the range from bone dry to about 100 ppm.

2. The process of claim 1, wherein the first catalyst component comprises between about 30 percent and about 70 percent of the total catalyst components.

3. The process of claim 1, wherein the catalyst produces an alkylated aryl compound having a 2-phenyl isomer content between about 15 percent and 45 percent, based on the weight of the alkylated aryl compound.

* * * * *